United States Patent
Frere

(10) Patent No.: US 9,518,910 B2
(45) Date of Patent: Dec. 13, 2016

(54) SMOKE DETECTION UNIT CONTAINING REDUNDANT DETECTORS AND METHOD FOR FIXING THE SMOKE DETECTION UNIT

(71) Applicant: SIEMENS AKTIENGESELLSCHAFT, Munich (DE)

(72) Inventor: Loic Frere, Versailles (FR)

(73) Assignee: Siemens Schweiz AG, Zurich (CH)

(*) Notice: Subject to any disclaimer, the term of this patent is extended or adjusted under 35 U.S.C. 154(b) by 185 days.

(21) Appl. No.: 14/564,607

(22) Filed: Dec. 9, 2014

(65) Prior Publication Data

US 2015/0160113 A1  Jun. 11, 2015

(30) Foreign Application Priority Data

Dec. 9, 2013 (EP) .................................... 13290306

(51) Int. Cl.
| | |
|---|---|
| G01N 15/06 | (2006.01) |
| G01N 33/00 | (2006.01) |
| G08B 17/10 | (2006.01) |
| G08B 29/16 | (2006.01) |
| G08B 17/113 | (2006.01) |
| G01N 15/00 | (2006.01) |

(52) U.S. Cl.
CPC .......... *G01N 15/06* (2013.01); *G01N 33/0036* (2013.01); *G08B 17/10* (2013.01); *G08B 17/113* (2013.01); *G08B 29/16* (2013.01); *G01N 2015/0046* (2013.01); *Y10T 29/49826* (2015.01)

(58) Field of Classification Search
CPC ............ G01N 15/06; G01N 2015/0046; G01N 33/0036; G08B 17/10; G08B 17/113; G08B 29/16
See application file for complete search history.

(56) References Cited

U.S. PATENT DOCUMENTS

| | | | |
|---|---|---|---|
| 4,254,414 A * | 3/1981 | Street ................... | G08B 17/00 264/555 |
| 2003/0062175 A1* | 4/2003 | Olander ................. | A62C 5/00 169/51 |
| 2004/0056765 A1 | 3/2004 | Anderson et al. | |
| 2005/0178539 A1* | 8/2005 | Rotta .................... | B64D 45/00 165/235 |
| 2006/0158327 A1* | 7/2006 | Fuchs ................... | G08B 17/10 340/531 |
| 2006/0267786 A1* | 11/2006 | Freiling .............. | G08B 17/113 340/628 |
| 2007/0103325 A1 | 5/2007 | Wagner et al. | |

* cited by examiner

*Primary Examiner* — Francis Gray
(74) *Attorney, Agent, or Firm* — Laurence Greenberg; Werner Stemer; Ralph Locher

(57) ABSTRACT

A smoke detection unit has two identical smoke detectors juxtaposed horizontally, each made up of at least one smoke sensor positioned beneath and coupled to a measuring chamber fitted with walls. The detectors are encapsulated in a rigid cavity having an upper base and a lower cover positioned opposite the smoke sensors. A base is formed by the walls of each of the two measuring chambers. A method further fixes the smoke detection unit to a bearing structure.

14 Claims, 2 Drawing Sheets

SMOKE DETECTION UNIT CONTAINING REDUNDANT DETECTORS AND METHOD FOR FIXING THE SMOKE DETECTION UNIT

CROSS-REFERENCE TO RELATED APPLICATION

This application claims the priority, under 35 U.S.C. §119, of European application EP 13 290 306.3, filed Dec. 9, 2013; the prior application is herewith incorporated by reference in its entirety.

BACKGROUND OF THE INVENTION

Field of the Invention

The present invention relates to a smoke detection unit containing redundant detectors.

A known smoke detection unit containing redundant detectors is shown in FIG. 1. Currently, such units are positioned in various places and in vehicles, such as aircraft, in particular in the cabin and above all in the hold so as to ensure a high level of smoke detection security if one of the detectors were to be defective. Mainly, such units are installed as a ceiling fitting element being housed in fitted structures such as false ceilings or other wall support structures.

Such units are also intended to detect various types of "smoke" in order to protect against specific external aggressions in a specific place, such as fire, saline mist, insecticide, etc. In fact, current smoke detectors provide for detection known as multi-criteria and the term "smoke" should be taken to mean a gas or a gas-liquid mixture affecting the atmosphere locally. Similarly, other types of detection are also possible, such as by detection/measurement of temperature or pressure as the case may be.

More precisely, according to the example in FIG. 1, such a smoke detection unit contains two identical smoke detectors 1, 2 juxtaposed horizontally. Each of the detectors 1, 2 being made up of at least one smoke sensor coupled to and positioned beneath a measuring chamber OC connected to an electronic module PCBa. The chamber is fitted with side and upper walls DCA, thus forming a protective casing for the chamber and the module. The detectors are finally encapsulated or assembled in a rigid cavity having an upper base CB and a lower cover CC. The lower cover CC is positioned opposite the smoke sensors and having here two sets of apertures DCO enabling the sensors to detect an ingress of smoke into the cavity.

The lower cover CC is fixed beneath an internal peripheral edge BO to the base and the upper base CB presents an external lip to the edge. The lip makes it possible to fix the complete detection unit onto a supporting structure such as one in the form of a ceiling fitting.

SUMMARY OF THE INVENTION

It is accordingly an object of the invention to provide a smoke detection unit containing redundant detectors and a method for fixing the smoke detection unit that overcome the above-mentioned disadvantages of the prior art devices and methods of this general type, wherein the dimensions and the weight of the unit are reduced.

Also, it is important to be able to associate this unit with an easy method for fixing into a bearing structure such as into a ceiling of a building or an internal wall of a vehicle/train/aircraft/etc.

With the foregoing and other objects in view there is provided, in accordance with the invention, a smoke detection unit. The smoke detection unit contains two identical smoke detectors juxtaposed horizontally and each have a measuring chamber with walls and at least one smoke sensor positioned beneath and coupled to the measuring chamber. A rigid cavity encapsulates the smoke detectors. The rigid cavity has an upper base and a lower cover positioned opposite the smoke sensors. The upper base is formed by the walls of the measuring chambers of the two identical smoke detectors.

In accordance with an added feature of the invention, the walls contain lower edges in contact with the lower cover. Ideally, the lower cover has two sets of apertures formed therein, and each of the sets of apertures is positioned directly opposite one of the smoke sensors.

In accordance with another feature of the invention, the lower cover has internal elements and the upper base contains two compartments which can be rigidly connected to the internal elements internal to the lower cover. The internal elements are independently detachable from the lower cover.

In accordance with an additional feature of the invention, the upper base and the lower cover has a material resistant to specific external aggressions in a place where the unit is present. Ideally the material resistant to specific external aggressions is glass fibers or carbon.

In accordance with a further feature of the invention, the rigid cavity has overall maximum dimensions of 480×480×60 mm. Furthermore the unit has a maximum weight of 1.5 kg.

In accordance with yet another feature of the invention, the smoke detectors form optical sensors which can be combined with other types of sensors such as of a gas, thermal, or pressure type.

In accordance with an added feature of the invention, the lower cover has a more extensive circumference than a circumference of the upper base.

Other features which are considered as characteristic for the invention are set forth in the appended claims.

Although the invention is illustrated and described herein as embodied in a smoke detection unit containing redundant detectors and a method for fixing the smoke detection unit, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DETAILED DESCRIPTION OF THE INVENTION

Figure 2A:
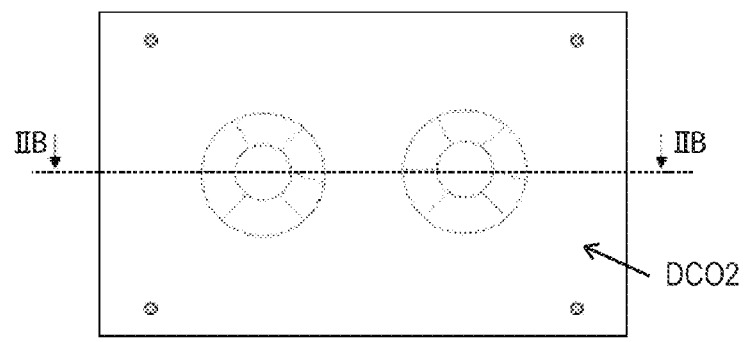
FIG. 2A is a bottom plan view of a first detection unit according to the invention taken along the line IIB-IIB of FIG. 2B.
Figure 2B:
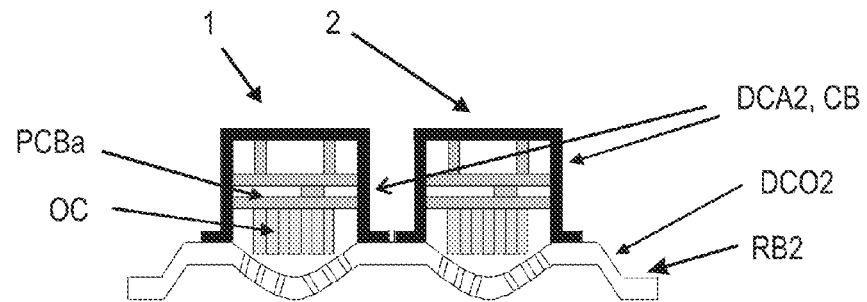
FIG. 2B is a front cross-sectional view of the first detection unit according to the invention.

Referring now to the figures of the drawings in detail and first, particularly to FIGS. 2A and 2B thereof, there is shown respectively a bottom view and a frontal cross-sectional view taken along the line IIB-IIB shown in FIG. 2B of a first detection unit according to the invention containing a one-piece cover.

The smoke detection unit contains two identical smoke detectors 1, 2 juxtaposed horizontally, each made up of at least one smoke sensor positioned beneath and coupled to a measuring chamber OC fitted with side and upper walls DCA, DCA2. The detectors are encapsulated in a rigid cavity having an upper base CB and a lower cover CC, DCO, DCO2 positioned opposite the smoke sensors, the invention provides that the upper base CB is exclusively formed by the walls DCA2 of each of the two measuring chambers.

Figure 1:
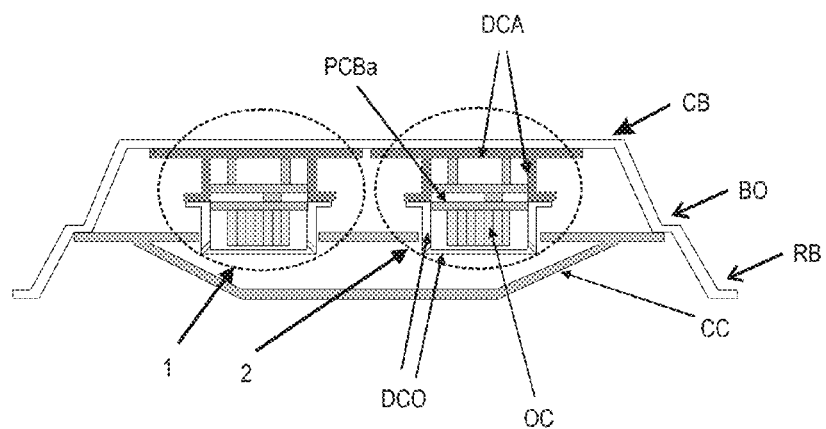
FIG. 1 is a diagrammatic, front view of a smoke detection unit according to the prior art.

In this way, a large base CB as presented in FIG. 1 can be avoided or at least considerably reduced in size and in weight, since it is advantageously replaced by the existing walls of the measuring chambers CO. Thus also, the overall size (initially given by the dimensions of the large base CB as presented in FIG. 1 of the unit according to the invention is thus reduced and the same goes for its weight.

By way of example, the cavity has overall maximum dimensions of 480×480×60 mm and the maximum weight of the unit is of the order of 1.5 kg.

The upper base CB in the form of the walls DCA2 also contains a material resistant to specific external aggressions (fire, saline mist, insecticide, etc.) in the place where the unit is present, in particular this material may be glass fiber or carbon, which makes it possible considerably to reduce the weight of the base/walls. The same may apply for the lower cover DCO2 which contains a material resistant to specific external aggressions (fire, saline mist, insecticide, etc.) in the place where the unit is present, in particular glass fiber or carbon.

The smoke detectors generally contain optical sensors of low mass and are able to be combined with other types of sensors such as of the gas, thermal, pressure, etc. type, depending on the needs of the desired detection.

It should be noted that, advantageously, the lower cover DCO2 has a more extensive circumference RB2 than a circumference of the upper base DCA2. It is by this circumference that it is possible to fix the complete detection unit to a holding position such as in the form of a ceiling fitting. However, bearing in mind that FIGS. 1 and 2A, 2B are approximately on the same scale, it can easily be seen that the size of the circumference RB2 in FIG. 2B is smaller than the size of the upper base CB in FIG. 1. This therefore means a reduction in size and weight of benefit both to the cover and to integration into a tighter holding structure as is often the case in particular in vehicles of all types (car, train, aircraft, holds, etc.).

Similarly to this latter advantage, a method for fixing the detection unit according to the invention is greatly facilitated in that a simple and light fixing of reduced size onto a bearing structure, in particular of the ceiling fitting type is performed by rigidly connecting parts on the circumference RB2 of the cover DCO2 onto at least one corresponding edge of the structure.

In order that the unit according to the invention remains as compact as possible, the side walls DCA2 contain lower edges in direct contact with the cover. Thus, the unit presents a minimum number of components forming the lightweight cavity.

Finally, the cover has two sets of apertures, each of the sets being positioned directly opposite one of the smoke sensors.

Figure 3A:
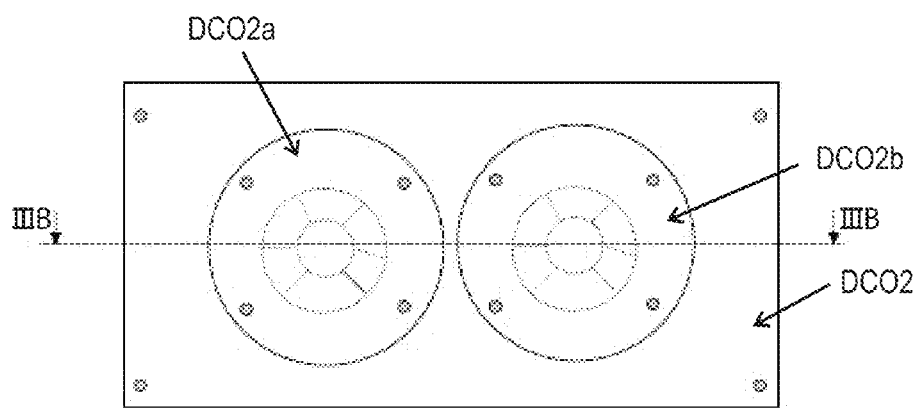
FIG. 3A is a bottom plan view of a second detection unit according to the invention taken along the line IIIB-IIIB.
Figure 3B:
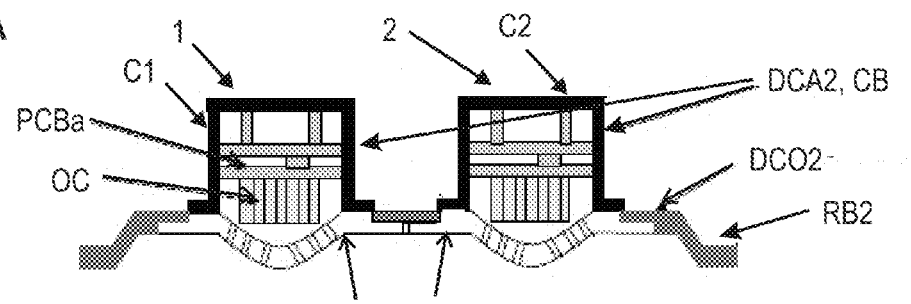
FIG. 3B is a front cross-sectional view of a second detection unit according to the invention.

FIGS. 3A and 3B present respectively a bottom view and a front cross-sectional view taken along the line IIIB-IIIB shown in FIG. 3A of a second detection unit according to the invention containing a three-piece cover DCO2.

In principle, all the characteristics of FIGS. 2A and 2B described above are common with those of FIGS. 3A, 3B.

In FIGS. 3A and 3B, it should be noted that the upper base CB, i.e. the two sets of walls DCA2 of each of the measuring chambers, forms two compartments C1, C2 which can be rigidly connected to parts (elements) internal DCO2a, DCO2b to the lower cover DCO2. The parts are in particular independently detachable from the lower cover DCO2. The cover thus has a three-piece structure instead of a single one-piece structure as in FIGS. 2A, 2B. The advantage associated with this aspect is the ability more simply to detach just one of the detectors (for example to change it, if a defect is signaled/found in one of the redundant detectors) without having to open the entire cavity.

The invention claimed is:

1. A smoke detection unit, comprising:
   two identical smoke detectors juxtaposed horizontally and each having a measuring chamber with walls and at least one smoke sensor positioned beneath and coupled to said measuring chamber; and
   a rigid cavity encapsulating said smoke detectors, said rigid cavity having an upper base and a lower cover positioned opposite said smoke sensors, said upper base is formed by said walls of said measuring chambers of said two identical smoke detectors.

2. The unit according to claim 1, wherein said walls contain lower edges in contact with said lower cover.

3. The unit according to claim 1, wherein said lower cover has two sets of apertures formed therein, each of said sets of apertures being positioned directly opposite one of said smoke sensors.

4. The unit according to claim 1, wherein:
   said lower cover having internal elements; and
   said upper base contains two compartments which can be rigidly connected to said internal elements internal to said lower cover, said internal elements being independently detachable from said lower cover.

5. The unit according to claim 1, wherein said upper base has a material resistant to specific external aggressions in a place where the unit is present.

6. The unit according to claim 1, wherein said lower cover has a material resistant to specific external aggressions in a place where the unit is present.

7. The unit according to claim 1, wherein said rigid cavity has overall maximum dimensions of 480×480×60 mm.

8. The unit according to claim 1, wherein the unit has a maximum weight of 1.5 kg.

9. The unit according to claim 1, wherein said smoke detectors form optical sensors which can be combined with other types of sensors such as of a gas, thermal, or pressure type.

10. The unit according to claim 1, wherein said lower cover has a more extensive circumference than a circumference of said upper base.

11. The unit according to claim 5, wherein said material resistant to specific external aggressions is selected from the group consisting of glass fiber and carbon.

12. The unit according to claim 6, wherein said material resistant to specific external aggressions is selected from the group consisting of glass fiber and carbon.

13. A method for fixing a smoke detection unit, which comprises the steps of:

providing a smoke detection unit containing two identical smoke detectors juxtaposed horizontally and each having a measuring chamber with walls and at least one smoke sensor positioned beneath and coupled to the measuring chamber and a rigid cavity encapsulating the smoke detectors, the rigid cavity having an upper base and a lower cover positioned opposite the smoke sensors, the upper base formed by the walls of the measuring chambers of the two identical smoke detectors; and fixing the smoke detection unit to a bearing structure by rigidly connecting parts on a circumference of the lower cover onto at least one corresponding edge of the bearing structure.

14. The method according to claim 13, which further comprises fixing the detection unit to a ceiling.

* * * * *